US010398155B2

(12) United States Patent
Rogge et al.

(10) Patent No.: US 10,398,155 B2
(45) Date of Patent: Sep. 3, 2019

(54) ANIMAL FEED COMPRISING A COMBINATION OF MONO GLYCERIDES

(71) Applicant: Proviron Holding N.V., Hemiksem (BE)

(72) Inventors: Tina Rogge, Hemiksem (BE); José Vanheule, Hemiksem (BE)

(73) Assignee: PROVIRON HOLDING N.V., Hemiksem (BE)

( * ) Notice: Subject to any disclaimer, the term of this patent is extended or adjusted under 35 U.S.C. 154(b) by 150 days.

(21) Appl. No.: 15/037,979

(22) PCT Filed: Nov. 20, 2014

(86) PCT No.: PCT/EP2014/025019
§ 371 (c)(1),
(2) Date: May 19, 2016

(87) PCT Pub. No.: WO2015/074767
PCT Pub. Date: May 28, 2015

(65) Prior Publication Data
US 2016/0286836 A1    Oct. 6, 2016

(30) Foreign Application Priority Data
Nov. 20, 2013  (BE) .................................. 2013/0781

(51) Int. Cl.
| A23K 20/158 | (2016.01) |
| A23K 50/75  | (2016.01) |
| A61K 31/23  | (2006.01) |
| A61K 9/00   | (2006.01) |
| A61K 9/16   | (2006.01) |
| A61K 31/22  | (2006.01) |

(52) U.S. Cl.
CPC ............ *A23K 20/158* (2016.05); *A23K 50/75* (2016.05); *A61K 9/0056* (2013.01); *A61K 9/1611* (2013.01); *A61K 31/22* (2013.01); *A61K 31/23* (2013.01)

(58) Field of Classification Search
None
See application file for complete search history.

(56) References Cited

U.S. PATENT DOCUMENTS

| 3,952,107 | A   |   | 4/1976  | Shibata       |           |
|-----------|-----|---|---------|---------------|-----------|
| 4,824,686 | A   | * | 4/1989  | Dunn ........  | A23K 30/00 |
|           |     |   |         |               | 252/380   |
| 5,565,232 | A   |   | 10/1996 | Wheeler et al.|           |
| 2004/0062847 | A1 |  | 4/2004  | Koike et al.  |           |

FOREIGN PATENT DOCUMENTS

| CN | 102696883 A   | 10/2012 |              |
|----|---------------|---------|--------------|
| DE | 19718245 C1   | 7/1998  |              |
| EP | 0089376 A1 *  | 9/1983  | ...... A23K 20/158 |
| EP | 0445692 A2    | 9/1991  |              |
| EP | 0519458 A1    | 12/1992 |              |
| EP | 1224870 A1    | 7/2002  |              |
| EP | 1342419 A1    | 9/2003  |              |
| JP | 3034678 B2    | 3/1993  |              |
| WO | 9513062 A1    | 5/1995  |              |
| WO | 0177271 A2    | 10/2001 |              |
| WO | 2006085346 A1 | 8/2006  |              |

OTHER PUBLICATIONS

International Preliminary Report on Patentability, dated May 24, 2016 from counterpart International Application PCT/EP2014/025019 filed Nov. 20, 2014. Six pages.

Antongiovanni, M. et al., "Butyric Acid Glycerides in the Diet of Broiler Chickens: Effect on Gut Histology and Carcass Composition," Italian Journal of Animal Science, vol. 6, No. 1, pp. 19-25, Jan. 1, 2007. Eight pages.

Antongiovanni, M. et al., "Monobutyrine: a Novel Feed Additive in the Diet of Broiler Chickens," Italian Journal of Animal Science, vol. 9, No. 4, Nov. 3, 2010.

Batovska, D. et al., "Antibacterial Study of the Medium Chain Fatty Acids and Their 1-Monoglycerides: Individual Effects and Synergistic Relationships," Polish Journal of Microbiology, vol. 58, No. 1, pp. 43-47, Jan. 1, 2009.

Skrivanova, E. et al., "Susceptibility of the *Escherichia coli, Salmonella* sp. and Clostridium perfringens to Organic Acids and Monolaurin," Veterinarni Medicina, vol. 51, No. 3, pp. 81-88, Jan. 1, 2006.

International Search Report and Written Opinion of the International Searching Authority, dated Jan. 13, 2015, from International Application No. PCT/EP2014/025019, filed on Nov. 20, 2014. Nine pages.

Search Report from Belgium Application No. BE 201300781, filed on Nov. 20, 2013. Two pages.

* cited by examiner

*Primary Examiner* — Robert T. Crow
*Assistant Examiner* — John P Nguyen
(74) *Attorney, Agent, or Firm* — HoustonHogle LLP

(57) ABSTRACT

The invention relates to a composition for admixture to animal feed or to the drinking water for animals, comprising monolaurate and monobutyrate glycerides, not comprising monoglycerides derived from a carboxylic acid having from 8 to 10 carbon atoms. The invention also relates to the use of this composition 1 as growth promoter in animal feed, preferably in poultry feed, still more preferably in broiler feed.

13 Claims, No Drawings

ANIMAL FEED COMPRISING A COMBINATION OF MONO GLYCERIDES

RELATED APPLICATIONS

This application is a § 371 National Phase Application of International Application No. PCT/EP2014/025019, filed on Nov. 20, 2014, which claims priority to Belgium Patent Application No. 2013/0781, filed on Nov. 20, 2013, both of which are incorporated herein by reference in their entirety.

FIELD OF THE INVENTION

The present invention relates to a composition for admixture to animal feeds, wherein such composition comprises a specific combination of mono glycerides. More in particular the composition of the present invention can advantageously be used in animal feeds for poultry, more in particular broiler-chicken.

The specified combination of monoglyceride compounds exhibits a surprising synergistic effect relating to the enhancement of the healthy growth of poultry.

BACKGROUND OF THE INVENTION

It is generally known that the efficacy of animal feeds may be enhanced by the addition of glycerol and or glycerol-ester compounds.

These added compounds may enhance such efficacy in various ways.

One of the aims pursued by such addition are the beneficial effects obtained in the stomach, resp. the intestinal tract of the animals fed.

It is known to the person skilled in the art to add in view of the above aim for example glycerol ester compositions derived from butyric acid.

STATE OF THE PRIOR ART

WO 2010/106488

The international patent application WO 2010/106488, inventor Fernando Cantini, published on Sep. 23, 2010, discloses the use of compositions on the basis of a combination of on the one hand glycerol and on the other hand mono glycerides derived from short chain fatty acids.

The compounds disclosed in this specification are being added as ingredients to animal feeds so as to counter the negative effects of moulds and bacteria that are formed in animal feed. In this way these compounds positively influence the results obtained by the use of these animal feeds.

The compositions described herein generally contain approximately 50% of glycerol, the remaining 50% being mono-, di- or triglycerides of for example butyric acid or propionic acid.

By the addition of such compounds the following beneficial effects are envisaged by the consumption of animal feeds comprising these compounds: improvement of the health of the intestinal tract and a reduction of the sensitivity of the animals for bacterial infections.

As specific compounds are mentioned mono/di/tri glycerides of fatty acids comprising three to fourteen carbon atoms.

These beneficial effects have been observed in particular when triglycerides of butyric acid are used, referred to as glycerol tri butyrate, abbreviated further as GTB. The GTB product is used in animal feeds as a functional ingredient and the concentration of the active ingredient is in the order of 2 to 4 kg/Ton of animal feed.

In particular this ingredient is added in animal feeds for chicken (laying hens as well as chicken grown for human feed (broilers)), veal and pigs.

WO 2006/085346 A1

The international patent application WO 2006/085346 A1, applicant and inventor Fernando Cantini, published on Aug. 17, 2006, discloses the use of mixtures of fatty acid glycerides from $C_1$ to $C_{22}$ to improve the zoo technical performances and/or the health of the intestine of animals.

More in particular this document discloses that the use of glycerides containing both butyric acid and short and medium chain fatty acids from $C_1$ to $C_{12}$ in animal feed makes it possible to obtain, in addition to the antibacterial/bacteriostatic effect, an important nutritional value especially for young animals.

The glycerides disclosed in this document comprise mono-, di- as well as triglycerides, in the following percentages:
Monoglycerides: 0%-86%
Diglycerides: 0%-86%
Triglycerides: 0%-100%.

With respect to a mixture of glycerides of butyric acid, by way of example, the following data have been disclosed (page 5, lines 17-19 of this specification):
Monoglycerides of butyric acid: 20%-25%
Diglycerides of butyric acid: 47%-53%
Triglycerides of butyric acid: 25%-30%.

Jon J. Kabara:

Professor Jon J. Kabara, professor at the Michigan State University, USA, has described the beneficial effects of Lauricidin® on human health.

Lauricidin® is the commercial name for monolaurin, the mono glyceride form of lauric acid.

Kabara has discovered that monolaurin counters the propagation of bacteria, moulds, protozoa and viruses in the human organism.

According to the studies of Kabara and Hierzolzer (1982) monolaurin confers as well an antiviral as an antibacterial effect.

Surprisingly, monolaurin does not have an adverse effect on the desired good bacteria in the human body, but only counters the potentially pathogenic micro-organisms.

US 2012/0041065:

this US patent application, published on Feb. 16, 2012 under the publication number US 2012/0041065 in the name of Can Technologies, Inc., USA, describes the effect of Lauric acid-distillate in animal feed.

Lauric acid distillate is produced as a by-product in the distillation process of pure vegetable oil derived from e.g. cocos oil.

More purified lauric acid distillate may be obtained by the further hydrolysis and distillation of this distillate, whereby as well mono-, di- as triglycerides are further processed to glycerol and free fatty acid. Reference is being made to paragraph (0005) of this specification.

The use of this lauric acid distillate, whether or not in combination with other additives, leads to an improved process for amongst other elements the growth of cattle.

This patent application deals only with lauric acid distillate; monolaurin has not been disclosed in this specification.

U.S. Pat. No. 5,462,967:

U.S. Pat. No. 5,462,967, issued on Oct. 31, 1995 to Kao Corporation, Tokyo, Japan, describes a composition for being added to animal feed, in particular for broilers, on the basis of a mixture of a triglyceride and either a mono- or a diglyceride of a medium-chain fatty acid. By medium chain fatty acid in the context of this specification is understood a fatty acid comprising between 6 and 12 carbon atoms.

Such a composition would, contrary to the compositions disclosed earlier (such as e.g. described in the Japanese patent application JP-A-1-215247) not have a detrimental effect on the liver of the animals fed. The compositions as described in this patent that contain apart from the mono- or diglyceride always a triglyceride, would be particularly beneficial with respect to the reduction of the fat content of the animals so fed, and with respect to the enhancement of the bodily reserves against protozoiasis diseases of chicken in particular.

Publication: Veterinarni Medicina, 51, 2006 (3): 81-88: Susceptibility of *Escherichia coli, Salmonella* sp. And *Clostridium perfringens* to organic acids and monolaurin.

This article describes the antibacterial functioning of fatty acids of C2 to C18 (Page 82, column 1 at the bottom) on various bacteria. Butyric acid and monolaurin have been cited, apart from other monoglycerides of medium chain length.

Publication: Applied and Environmental Microbiology, January 2006, p. 522-526.

Stable concentrated emulsions of 1-Monoglyceride of Capric Acid (monocaprin) with microbicidal activities against the food-borne bacteria . . . .

This article again confirms the antibacterial functioning of fatty acids of a.o. 1-monoglyceride of capric acid (monocaprin), monolaurin or lauric acid.

Publication: Antimicrobial Agents and Chemotherapy, March 1992, p. 626-631

Effect of glycerol monolaurate on bacterial growth and toxin production.

Also this study deals with the antibacterial functions of monolaurin or glycerol monolaurate.

Publication: PSP Volume 27-No 3, 2005, Advances in Food Sciences (AFS)

Effect of low doses of monolaurin on growth of common foodborne microbial strains.

Also this article describes the antimicrobial effect of glycerol monolaurate against various types of bacteria, as well the Gram-positive as Gram-negative types.

Publication: Applied and Environmental Microbiology, February 1992, p. 624-629, American Society for Microbiology:

Inhibition of *Listeria monocytogenes* by Fatty Acids and Monoglycerides.

Also this article describes the inhibiting effect of various monoglycerides, such as monolaurin, in dairy products, for example creamy or skimmed milk.

Publication: Polish Journal of Microbiology, 2009, Vol. 58, No. 1, 43-47:

Antibacterial Study of the Medium Chain Fatty Acids and their 1-monoglycerides: individual effects and synergistic relationships.

Also in this article the antibacterial activity of aliphatic fatty acids of medium chain length is described, and in particular lauric acid (C-12).

This effect is enhanced when the acid is esterified by glycerol resulting in monolaurin. Monolaurin has been described as particularly effective against a.o. Gram-positive pathogenic bacteria. The spectrum of its activity can be further enlarged when it is used in combination with other substances, for instance with a cathion-chelator such as EDTA. Further synergistic effects are described when monolaurin is combined with a number of other compounds that may be added such as phosphates, antioxidants and feeding acids.

Synergistic effects also have been observed when monolaurin is combined with monocaprin, as well as in combination with lauric acid. The latter compound is less active if used alone.

Problem to be Solved

It is known that animals, in particular broiler, can be fed quickly and efficiently up to the point at which they can be slaughtered, provided antibiotics are added to the feed or to the drinking water. An example of such known antibiotic compound is Tylvalosin, abbreviated to TVN.

This product has been described e.g. in the International PCT patent publication WO2008/007104A1, applicant ECO Animal Health Ltd. & Cambridge University Technical Services, U.K.

Until 2006 in principle, certain growth promoters could be used in Europe, but in view of the presence of problems due to the resistivity of organisms, such as e.g. the MRSA-bacteria (Methicillin Resistant Staphylococcus Aureus), these kind of products have been banned. The occurrence in the Netherlands of the ESBL-enzymes (Extended Spectrum Beta-Lactamase) resulted in an accelerated reduction, namely a total reduction of the use of antibiotics with 50% by the end of 2013, and most probably a further reduction for the period beyond 2013.

Although in larger parts of the world, in particular outside Europe, these kind of products may still be used, the industry at large performs substantive efforts to develop fully-functional alternate compounds for promoting the growth of animals.

More in particular these efforts are directed to the development of feed-ingredients that cause a conversion of feed to meat in the most efficient manner. Differently phrased, the aim is to assure that the animal, for a given amount of animal feed, is characterized by an increase of weight as high as possible, since this is an direct measure of the amount of animal meat.

However in the realization of this aim, care should be taken of the health of the animals fed. In particular the animal should remain free of viral or bacterial infections, without feeding antibiotics to the animal.

In practice, it appears to be difficult to develop compositions for admixture to animal feed that at the same time enable a quick and efficient growth of the animal, without having to recur to the use of antibiotics, and whereby still the health of the animal, in particular the absence of viral or bacterial infections, remains of primary concern.

AIM OF THE INVENTION

The aim of the present invention is to remedy the above and other problems. More in particular the aim of the inventors is the development of compositions that when added to animal feed, positively contribute to the growth of animals, without adverse effect on their health, and without the need to add antibiotics. More in particular the aim of the inventors is the development of compositions for enhancing the growth of animals, without adverse effects on the viral or bacterial health of the animals fed.

SUMMARY OF THE INVENTION

After many experiments and tests the present inventors have found that the abovementioned problems effectively may be avoided, and the abovementioned aims may be achieved by the development of compositions and feeds as specified in the claims included in the present specification.

Also animal feeds for the improvement of the growth of animals, comprising such compositions, are the subject of the present invention.

Preferred embodiments of the invention are set forth in the dependent claims of the present specification, as well as in the detailed description of the invention set forth hereinafter.

DETAILED DESCRIPTION OF THE INVENTION

The inventors have performed various experiments and tests whereby various compounds, in varying weight ratios, have been added to animal feeds, and their effects on the growth as well on the health of animals were noted.

These tests in particular were performed on animal feed to be consumed by poultry, more in particular poultry intended for human consumption, hereinafter referred to as broilers.

The results of these tests however are equally applicable to hoofed animals such as pigs, cows, horses, or to shell- or cray-fish, such as shrimps, scampi, oysters, mussels, clams, etc.

Tests Performed:

Tests have been performed with a large number of products, known per se. As will be apparent from the description hereinafter, surprisingly good results have been achieved for a combination of two products, provided the synergistic effect obtained by the combined used of these compounds is not inhibited by the presence in the animal feed of certain other products.

The products that yield, under specified conditions, a synergistic effect, are the following:

on the one hand, use was made of monolaurin, this is glycerol monolaurate;
on the other hand, use was made of monobutyrin, this is glycerol butyrate.

Monolaurate as well as monobutyrate are monoglycerides.

These products may be obtained e.g. by the esterification of glycerol with the corresponding carboxylic acid, resp. lauric acid and butyric acid, followed by a purification step in order to remove the excess of raw materials that were used.

The esterification of the alcohol, in this case glycerol, with the organic acid takes place according to the reaction mechanism set forth herein below:

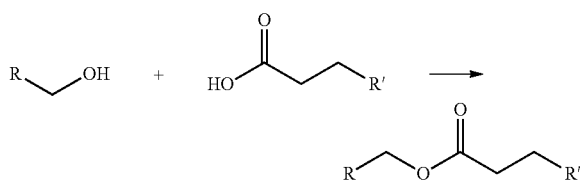

The structural formulae of butyric acid and lauric acid are as follows:

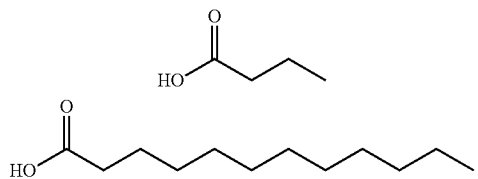

The structural chemical formulae of the monolaurate, resp. the monobutyrate is as follows:

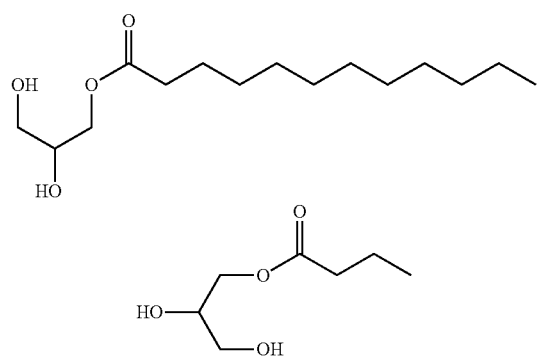

Butyric acid is a carboxylic acid comprising 4 carbon atoms, whereas lauric acid is a carboxylic acid comprising 12 carbon atoms.

In the tests set forth hereinafter use has been made also of the esterification product of glycerol with caprylic acid, resp. capric acid. These are carboxylic acids comprising 8, resp. 10 carbon atoms.

Their structural formulae is set forth below:

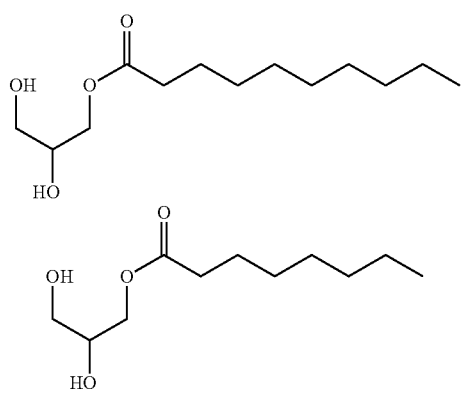

The results obtained when each of these compound was used alone, was more or less as expected. However, a surprising and unexpected synergistic effect was obtained when monolaurin and monobutyrate were used in combination. Still more surprising, the inventors noted that these synergistic effect was to a large effect inhibited when particular monoglyceride compounds were used together with this synergistic combination of compounds.

No scientific explanation can be given for this inhibitive effect.

The tests were performed as follows:

Broiler chicken were grown during 42 days, with and without the abovementioned compositions being added to either the animal feed, or the drinking water.

By the end of the test period of 42 days, the final weight of the broiler was determined, this is the AEW (Average End Weight), as well as the degree of conversion of feed to chicken weight, this is the FCR (Feed Conversion Rate). The latter parameter indicates the amount of feed a broiler chicken should eat per kilogram of final weight of the animal. The lower this parameter, the more efficient the chicken has been fed. This parameter is influenced by the way the animal feed is digested by the intestinal tract or metabolism of the chicken, but also by the way the feed offered to the chicken is effectively accepted by the animal. The latter to a large extent is determined by the taste of the feed offered. To the extent the taste of the feed offered is positively acknowledged by the chicken, less feed is removed by the animal; so dependent on the taste of the feed, more or less of the feed is discarded by the chicken.

During the tests, various treatments have been carried out.

These treatments are summarized in the table set forth hereinafter.

The tests were performed on groups of each time 20 broilers for each pen.

Each test was repeated on each time five pens, so each test was performed on in total 100 broilers.

The results of these tests are shown in the following table. Each value represents an average amount of the results obtained for each set of the five pens.

These results relate to the following parameters:

Average final weight of the broilers at day 42 (AEW);

Degree of conversion of feed into chicken weight (FCR) measured over the entire period.

The results are summarized in the following table:

| Number | additive | Dosage Kg/Ton | D 0-42 AEW | Ranking AEW 42 | D 0-42 FCR | Ranking FCR 42 |
|---|---|---|---|---|---|---|
| Ref 1 | Poor feed | | 2.40 | 91% | 1.77 | 106.1% |
| Ref 2 | Rich feed | | 2.64 | 100% | 1.66 | 100.0% |
| Ref 3 | TVN 5 mg/KgLW via drinking water | 0.04 | 2.79 | 106% | 1.61 | 96.6% |
| Comp 1 | monolaurin | 2.4 | 2.65 | 101% | 1.69 | 101.3% |
| Comp 2 | monolaurin | 1.2 | 2.55 | 97% | 1.74 | 104.6% |
| Comp 3 | monolaurin + monoglyceride C8-C10 (50%/50%) | 4 | 2.59 | 98% | 1.67 | 100.5% |
| Comp 4 | monobutyrin | 2 | 2.68 | 102% | 1.63 | 97.9% |
| Comp 5 | monobutyrin | 4 | 2.63 | 100% | 1.70 | 101.9% |
| Comp 6 | monobutyrin via drinking water | 2.22 | 2.65 | 101% | 1.64 | 98.6% |
| Comp 7 | monobutyrin + monoglyceride C8-C10 (50%/50%) | 4 | 2.65 | 101% | 1.64 | 98.8% |
| Comp 8 | monobutyrin + monolaurin + monoglyceride C8-C10 (each 33.33%) | 6 | 2.71 | 103% | 1.59 | 95.6% |
| Comp 9 | monoglyceride C8-C10 | 2.2 | 2.65 | 101% | 1.64 | 98.8% |
| Comp 10 | monoglyceride C8-C10 | 4.4 | 2.62 | 100% | 1.68 | 101.1% |
| Comp 11 | monoglyceride C8-C10 | 4.4 | 2.51 | 95% | 1.74 | 104.5% |
| Example 1 | Monobutyrin + monolaurin 50%/50% | 4 | 2.85 | 108% | 1.59 | 95.6% |
| Example 2 | Monobutyrin + monolaurin 65%/35% | 4 | 2.90 | 110% | 1.61 | 97.1% |
| Example 3 | Monobutyrin + monolaurin 35%/65% | 4 | 2.79 | 106% | 1.61 | 96.7% |
| Example 4 | Monobutyrin + monolaurin 50%/50% | 2 | 2.69 | 102% | 1.65 | 99.1% |
| Example 6 | Monobutyrin + monolaurin 65%/35% | 2 | 2.75 | 104% | 1.64 | 98.7% |
| Example 7 | Monobutyrin + monolaurin 35%/65% | 2 | 2.67 | 101% | 1.66 | 99.7% |

The meaning of the various columns of this table is as follows:

The first column shows the reference number of the test performed.

The second column (additive) shows the composition of the additives used in the test under consideration, as well as the ratio of these additives in weight percentages.

The third column (Dosage kg/ton) shows how much of this composition has been added to the feed, expressed in kg of the composition concerned per ton of animal feed.

In a number of cases the composition has been added to the drinking water of the animal; in such a case the composition enters the intestinal tract of the animal by drinking.

In case monobutyrin is added to the feed, then this compound preferably is first added to an inert carrier such as silica. It is then added to the feed as a powdery compound. In practice it is much easier to mix such a powdery composition with the animal feed, as compared to the addition of a fluid to the feed.

The next two columns show the results of the test, expressed as final weight of the animal, in this case a broiler chicken.

The column with the heading D 0-42 AEW denotes the average final weight of the broilers at day 42 (Average End Weight). The higher the value for this parameter, the better.

The column with the title Ranking AEW 42 denotes, expressed as a percentage, the result of the test in terms of AEW, as compared to the standard test, corresponding to a standard value set at 100%.

The last two columns set forth the results of the test, expressed differently, namely as a measure for the conversion of the feed in meat-resp. increase of weight of the animal, as set forth above.

The column with the title D 0-42 FCR denotes the average value of the conversion of feed to weight of the animal. The lower the value for this parameter, the better. The lower the value, the more efficient the conversion of feed into animal meat has been performed.

The column with the heading Ranking FCR 42 denotes, expressed as a percentage, the result of the test with respect to FCR, as compared to the standard test, which has been allocated the value of 100%.

Discussion of the Test Results:

The feed that has been fed to the broilers in the various tests comprises two different embodiments:

a first type of feed is the so-called 'Poor Feed': this is a normal, customary feed that is being fed to the broilers, whereby no forced growth and feed conversion is to be expected, and whereby also no particular duty on the intestinal tract of the broilers is imposed. Differently phrased, the broilers have no difficulty in digesting this feed, and the younger broilers grow in a normal path to fully-grown adult animals.

a second type of feed is the so-called 'Rich Feed': this is a feed particularly high in energy and proteins, to which a component has been added that results in a more viscous intestine content. The result of the use of this type of feed is that the growth of the broilers is intensified, but it also results in a heavier load on the intestinal tract. So the intestines of the broilers should work harder to fully digest the feed absorbed by the animal. In this case the risk of disturbing the bacterial balance in the intestinal tract is substantially higher.

Such an imbalance in bacteria (dysbacteriosis) may be a cause of diseases with resulting adverse effects.

These tests clearly show on the one hand that the combined use of monolaurin and monobutyrin unexpectedly yields synergistic effects.

The effects obtained by this synergistic mixture even exceed the results of the test wherein antibiotics—meanwhile forbidden in Europe—are used in the animal feed!

However these tests (see in particular test nr. 8) also clearly demonstrate that the beneficial effects to a large extent are annulled or inhibited as soon as a fatty acid monoglyceride having 8 to 10 carbon atoms is added to such synergistic mixture, or as soon as a mixture of such fatty acid monoglycerides is added.

In the test denoted 'Poor Feed', over the entire test period of 42 days, 'Poor Feed' was fed to the broilers. The results of this test were inferior to all of the tests performed. The average end weight of the broilers after 42 days amounted to 2.40 kg, corresponding to a feed efficiency of 1.77.

In the test denoted 'Rich Feed' during the first thirteen days 'Poor Feed' was offered to the broilers. In the subsequent period—from day 14 to day 42—'Rich Feed' was fed.

The final weight of the broilers in this test has been increased to an average value of 2.64 kg and the feed efficiency amounted to 1.66.

So these results are substantially better as compared to the situation that the broilers are fed with the normal or poor feed over the entire period.

The risk corresponding to this type of feed however is the occurrence of diseases, as set forth above.

This test with the 'Rich Feed' is taken as the reference for the following tests. The columns 'Ranking AEW 42' and 'Ranking FCR 42' represent the results obtained for each test, measured as compared to this reference test, the value whereof is set at 100%.

In this way, the effect of the various compositions added to the animal feed in the various tests, is measured as compared to the results obtained in this 'standard' or reference test.

In each of the tests performed, the broilers are fed as in the standard test with 'Rich Feed'.

The first thirteen days they are fed with 'Poor Feed', and in the subsequent period up to the final day 42, they are fed with 'Rich Feed'.

To as well the 'Poor Feed' as the 'Rich Feed' in these tests, the compositions set forth in the various tests have been added to these animal feeds.

From the test with a 50% 50% combination of monolaurin and monobutyrin it appears that the result in terms of AEW is the highest, and expressed as a percentage as compared to the reference values from the standard test, it amounts to 107.93%, rounded off to 108%.

Similar results are obtained as illustrated by the other examples according to the invention (examples numbers 2-7).

The use of the antibiotic Tylvalosin only yields an improvement as compared to the reference value from the standard test of 105.53%, rounded of to 106% in the table.

The average increase in weight per day of the broilers clearly was above industry-average, and amounted to the following values:

57.2 gr in case of use of Poor Feed without addition of monoglycerides;

62.7 gr in case of use of Rich Feed without addition of monoglycerides;

66.3 gr in case of use of Rich Feed with addition of TVN.

The difference between poor and rich fee so amounted to 234 gr.

From the tests wherein monolaurin alone was added to the feed, it appears that the final weight of the broilers increased to the extent more of this compound is added to the feed. The final weight after 42 days for example increases from 2.55 kg to 2.65 kg in case 1.2 kg of monolaurin, resp. 2.4 kg of monolaurin has been added per one ton of feed.

The efficiency of feeding likewise increases, as illustrated by a steadily decrease of the FCR value to the extent more monolaurin has been added.

From the tests with monobutyrin, it appears that no corresponding improvement can be established, to the extent more of this ingredient has been added to the feed. The final weight of the broiler in this case indeed decreases from 2.68 kg to 2.63 kg when 2, resp. 4 kg of this compound has been added per ton of animal feed. Also the feeding efficiency decreases, as illustrated by an increase of the FCR value to the extent more monobutyrine is added to the feed.

So the more surprising is the unexpected synergistic effect that is obtained when both of these ingredients are added to the feed in the correct ratio. This is apparent from the results of the 50/50% test of both monoglycerides as well as from the test wherein the respective weight ratios between both glycerides amounts to 65/35%, 35/65% respectively.

However, still more surprising, this synergistic effect is to a very large extent inhibited or annulled when a fatty acid monoglyceride having 8 to 10 carbon atoms is used along with this synergistic combination of monoglycerides. See in this respect the results of test nr. 8.

According to a preferred embodiment, the compositions according to the invention comprise at least 50% of monobutyrin, e.g. 50 or 65%, as is apparent from tests nr. 1, 2 and 6.

Also, according to a preferred embodiment, the animal feed comprise the composition according to the invention in an amount of up to 10 kg per ton of feed, preferably between 3 and 5 kg per ton of feed. This is illustrated from the results shown in the examples numbered 1 to 3.

According to a further preferred embodiment of the invention, the composition according to the invention comprises an inert carrier whereupon one or both of said monoglycerides as individual components, or as a mixture has been deposited.

Such inert carrier may comprise or consist of silica (particles).

The invention claimed is:

1. A composition for admixture to animal feed or to the drinking water for animals, consisting of monolaurate glyceride and monobutyrate glyceride, obtained by the esterification of glycerol with the corresponding carboxylic acid, respectively lauric acid and butyric acid, followed by a purification step in order to remove the excess of raw materials that were used.

2. An animal-feed comprising the composition as defined in claim 1.

3. The animal feed of claim 2 further comprising an inert carrier whereupon both of said monoglycerides has been deposited.

4. The animal feed of claim 3 wherein the inert carrier comprises or consists of silica.

5. The animal feed of claim 2, wherein the composition is present in an amount of between three and five kilograms per ton of feed.

6. The animal feed of claim 5, wherein the composition is present in an amount of about four kilograms per ton of feed.

7. A composition for admixture to animal feed or to the drinking water for animals, consisting of monolaurate glyceride and monobutyrate glyceride, obtained by the esterification of glycerol with lauric acid and butyric acid respectively, followed by a purification step in order to remove the excess of raw materials that were used, wherein the weight ratio of the monolaurate glyceride to monobutyrate glyceride is between 65/35 and 35/65.

8. An animal-feed comprising the composition of claim 7.

9. The composition of claim 7 wherein the weight ratio of the monolaurate glyceride to monobutyrate glyceride is between 60/40 and 40/60.

10. The composition of claim 7 wherein the weight ratio of the monolaurate glyceride to monobutyrate glyceride is about 50/50.

11. The animal-feed of claim 8 further includes an inert carrier whereupon both of said monoglycerides has been deposited.

12. The composition of claim 11 wherein the inert carrier comprises silica.

13. The animal feed of claim 8, comprising the composition in an amount of up to 10 kg per ton of feed.

* * * * *